(12) United States Patent
Furman (10) Patent No.: US 8,298,148 B2
(45) Date of Patent: Oct. 30, 2012

(54) INTEGRATED HEART MONITORING DEVICE AND METHOD OF USING SAME

(75) Inventor: Dan Gur Furman, Gedera (IL)

(73) Assignee: Cardio Art Technologies Ltd, Or Yehuda (IL)

( * ) Notice: Subject to any disclaimer, the term of this patent is extended or adjusted under 35 U.S.C. 154(b) by 1111 days.

(21) Appl. No.: 12/119,325

(22) Filed: May 12, 2008

(65) Prior Publication Data

US 2008/0249379 A1    Oct. 9, 2008

Related U.S. Application Data (63) Continuation-in-part of application No. PCT/IL2006/001416, filed on Dec. 10, 2006.

(60) Provisional application No. 60/748,218, filed on Dec. 8, 2005.

(30) Foreign Application Priority Data

Aug. 30, 2007 (IL) .......................................... 185609

(51) Int. Cl.
   *A61B 8/00* (2006.01)
   *A61B 5/02* (2006.01)
(52) U.S. Cl. ........ 600/453; 600/374; 600/465; 600/485; 600/504
(58) Field of Classification Search .................. 600/374, 600/453, 465, 485, 504
   See application file for complete search history.

(56) References Cited

U.S. PATENT DOCUMENTS

| | | |
|---|---|---|
| 4,770,177 A | 9/1988 | Schroeppel |
| 5,113,869 A | 5/1992 | Nappholz et al. |
| 5,174,295 A | 12/1992 | Christian et al. |
| 5,218,962 A | 6/1993 | Mannheimer et al. |
| 5,309,916 A | 5/1994 | Hatschek |
| 5,409,009 A | 4/1995 | Olson |
| 5,464,434 A | 11/1995 | Alt |
| 5,488,953 A | 2/1996 | Vilkomerson |

(Continued)

FOREIGN PATENT DOCUMENTS

WO    WO 92/20273    11/1992

(Continued)

OTHER PUBLICATIONS

International Preliminary Report on Patentability on PCT Application No. PCT/IL2006/001416; issued Mar. 10, 2009; 7 pages; International Bureau of WIPO, Geneva, Switzerland.

(Continued)

*Primary Examiner* — Carl H Layno
*Assistant Examiner* — Natasha Patel
(74) *Attorney, Agent, or Firm* — Faegre Baker Daniels LLP (57) ABSTRACT

A device for monitoring the heart of a patient including a housing, a computing device, an optical sensor adapted to provide signals to the computing device indicative of a distance from the optical sensor to a vessel carrying blood, as well a diameter of the vessel, a Doppler sensor adapted to provide signals to the computing device indicative of a velocity of the blood through the vessel, and an ECG sensor adapted to provide signals to the computing device indicative of a plurality of electrical stimuli that cause the heart to pump. The computing device uses signals from the optical sensor, the Doppler sensor, and the ECG sensor to compute parameters including oxygen saturation of the blood, blood flow, blood pressure, heart rate, and cardiac output.

23 Claims, 7 Drawing Sheets

U.S. PATENT DOCUMENTS

| | | | |
|---|---|---|---|
| 5,544,649 | A | 8/1996 | David et al. |
| 5,558,092 | A | 9/1996 | Unger |
| 5,606,972 | A | 3/1997 | Routh |
| 5,713,939 | A | 2/1998 | Nedungadi et al. |
| 5,772,589 | A | 6/1998 | Bernreuter |
| 5,817,009 | A | 10/1998 | Rosenheimer et al. |
| 5,833,603 | A | 11/1998 | Kovacs et al. |
| 5,995,208 | A | 11/1999 | Sarge et al. |
| 6,053,873 | A | 4/2000 | Govari et al. |
| 6,176,832 | B1 | 1/2001 | Habu et al. |
| 6,206,835 | B1 | 3/2001 | Spillman, Jr. et al. |
| 6,231,516 | B1 | 5/2001 | Keilman et al. |
| 6,261,233 | B1 | 7/2001 | Kantorovich |
| 6,277,078 | B1 | 8/2001 | Porat et al. |
| 6,398,731 | B1 | 6/2002 | Mumm et al. |
| 6,475,153 | B1 | 11/2002 | Khair et al. |
| 6,485,418 | B2 | 11/2002 | Yasushi et al. |
| 6,609,023 | B1 | 8/2003 | Fischell et al. |
| 6,622,322 | B1 | 9/2003 | Caveney |
| 6,929,610 | B2 | 8/2005 | Forstner |
| 7,004,907 | B2 | 2/2006 | Banet et al. |
| 7,125,383 | B2 | 10/2006 | Hoctor et al. |
| 7,127,300 | B2 | 10/2006 | Mazar et al. |
| 7,179,228 | B2 | 2/2007 | Banet |
| 7,238,159 | B2 | 7/2007 | Banet et al. |
| 7,267,649 | B2 | 9/2007 | Zdeblick et al. |
| 7,272,428 | B2 | 9/2007 | Hopman et al. |
| 7,308,292 | B2 | 12/2007 | Colvin et al. |
| 7,396,330 | B2 | 7/2008 | Banet et al. |
| 2002/0010390 | A1 | 1/2002 | Guice et al. |
| 2002/0095092 | A1* | 7/2002 | Kondo et al. ............... 600/503 |
| 2003/0097068 | A1* | 5/2003 | Hossack et al. ............. 600/443 |
| 2003/0139778 | A1 | 7/2003 | Fischell et al. |
| 2004/0106953 | A1 | 6/2004 | Yomtov et al. |
| 2004/0167416 | A1* | 8/2004 | Lee ............................ 600/513 |
| 2004/0236223 | A1 | 11/2004 | Barnes et al. |
| 2005/0096557 | A1 | 5/2005 | Vosburgh et al. |
| 2005/0216199 | A1 | 9/2005 | Banet |
| 2005/0228299 | A1 | 10/2005 | Banet |
| 2005/0228300 | A1 | 10/2005 | Jaime et al. |
| 2005/0245831 | A1 | 11/2005 | Banet |
| 2005/0245882 | A1 | 11/2005 | Elkins et al. |
| 2005/0261594 | A1 | 11/2005 | Banet |
| 2006/0009697 | A1 | 1/2006 | Banet et al. |
| 2006/0009698 | A1 | 1/2006 | Banet et al. |
| 2006/0100530 | A1* | 5/2006 | Kliot et al. .................. 600/483 |
| 2006/0129038 | A1 | 6/2006 | Zelenchuk et al. |
| 2006/0224053 | A1 | 10/2006 | Black et al. |
| 2006/0253007 | A1 | 11/2006 | Cheng et al. |
| 2007/0088214 | A1* | 4/2007 | Shuros et al. ................ 600/437 |
| 2007/0093702 | A1 | 4/2007 | Yu et al. |
| 2007/0142715 | A1 | 6/2007 | Banet et al. |
| 2007/0185393 | A1 | 8/2007 | Zhou et al. |
| 2007/0244398 | A1 | 10/2007 | Lo et al. |
| 2007/0265533 | A1 | 11/2007 | Tran |
| 2007/0276261 | A1 | 11/2007 | Banet et al. |
| 2007/0276632 | A1 | 11/2007 | Banet et al. |
| 2007/0299318 | A1 | 12/2007 | Chen et al. |
| 2008/0027323 | A1 | 1/2008 | Freiburger |
| 2008/0077026 | A1 | 3/2008 | Banet et al. |
| 2008/0082004 | A1 | 4/2008 | Banet et al. |
| 2008/0114220 | A1 | 5/2008 | Banet et al. |
| 2008/0195043 | A1 | 8/2008 | Swach et al. |
| 2008/0221399 | A1 | 9/2008 | Zhou et al. |
| 2008/0221461 | A1 | 9/2008 | Zhou et al. |

FOREIGN PATENT DOCUMENTS

| | | |
|---|---|---|
| WO | WO 93/17621 | 9/1993 |
| WO | WO01/85014 | 11/2001 |
| WO | WO03/015838 | 2/2003 |
| WO | WO 2006/113748 | 10/2006 |
| WO | WO 2007/035934 | 3/2007 |
| WO | WO 2007/066343 | 6/2007 |
| WO | WO 2007/122375 | 11/2007 |

OTHER PUBLICATIONS

Office Action dated Dec. 22, 2010, in commonly owned U.S. Appl. No. 12/119,339.

International Search Report and the Written Opinion of the International Searching Authority for PCT/IB09/06088, Jul. 5, 2011, 9 pages.

Chemla et al., Blood flow acceleration in the carotid and brachial arteries of healthy volunteers: respective contributions of cardiac performance and local resistance, 1996, Fundam Clin Pharmacol, 10, pp. 393-399.

Tahmasebpour et al., Sonographic Examination of the Carotid Arteries, 2005, RadioGraphics, 25, pp. 1561-1575.

Office Action dated Oct. 7, 2011, in commonly owned U.S. Appl. No. 12/119,339, 20 pgs.

Office Action dated Dec. 21, 2011, in commonly owned U.S. Appl. No. 12/206,885, 14 pgs.

Office Action dated Dec. 13, 2011, in commonly owned U.S. Appl. No. 12/119,462, 9 pgs.

* cited by examiner

INTEGRATED HEART MONITORING DEVICE AND METHOD OF USING SAME

CROSS-REFERENCE TO RELATED APPLICATIONS

The present application claims priority to and is a continuation-in-part of patent application Ser. No. 185609 filed Aug. 30, 2007, titled "MULTI-FUNCTION SENSSOR," and International Patent Application No. PCT/IL2006/001416 filed Dec. 10, 2006, titled "IMPLANTABLE BIOSENSING DEVICE AND HEALTH MONITORING SYSTEM AND METHOD INCLUDING SAME," which claims the benefit of U.S. Provisional Patent Application Ser. No. 60/748,218 filed Dec. 8, 2005, titled "WIRELESS INTEGRATED TRANSMITTER AND SENSOR, the disclosures of which are expressly incorporated by reference herein.

The present application is related to U.S. Utility Patent Application Ser. No. (12/119,315) titled "OPTICAL SENSOR APPARATUS AND METHOD OF USING SAME" filed on even date herewith, (hereinafter, "the Optical Sensor Apparatus application"), U.S. Utility Patent Application Ser. No. (12/119,339) titled "DOPPLER MOTION SENSOR APPARATUS AND METHOD OF USING SAME" filed on even date herewith, (hereinafter, "the Doppler Motion Sensor application"), and U.S. Utility Patent Application Ser. No. (12/119,462) titled "METHOD AND SYSTEM FOR MONITORING A HEALTH CONDITION" filed on even date herewith, (hereinafter, "the System for Monitoring application"), the entire disclosure of each application being expressly incorporated by reference herein.

FIELD OF THE INVENTION

The present invention relates to sensing devices and, more specifically, to devices for monitoring cardiac behaviour.

BACKGROUND AND SUMMARY OF THE INVENTION

Cardiovascular disease is a large, growing health problem world wide. Some studies indicate that approximately 15% of the Western World suffers from one or more cardiovascular disease. In the United States, nearly 25% of the population is affected, resulting in more than six million hospitalizations every year.

Various devices exist for monitoring certain parameters relating to cardiac performance. In some instances, in vivo parameters of a patient may need to be monitored over a period of time; for example, such monitoring may be necessary in a subject who has occasional irregular cardiac beats. Heart arrhythmias are changes in the normal sequence of electrical impulses that cause the heart to pump blood through the body. As such abnormal heart rhythms may only occur sporadically, continuous monitoring may be required for detection. By providing continuous monitoring, medical personnel determine if there is a tendency for production of sustained irregular beats in a life-endangering fashion. Medical personnel also use the monitoring results to establish a proper course of treatment.

One prior art device that measures heart rate is the "Reveal" monitor by Medtronic (Minneapolis, Minn., USA). This device comprises an implantable heart monitor used, for example, in determining if syncope (fainting) in a subject is related to a heart rhythm problem. The Reveal monitor continuously monitors the rate and rhythm of the heart for up to 14 months. After waking from a fainting episode, the subject places a first recorder device external to the skin over the implanted Reveal monitor and presses a button to transfer data from the monitor to the recorder. The subject gives the first recorder to a physician who provides the subject with a second recorder to use for continued data acquisition. The physician then analyzes the information stored on the first recorder to determine whether abnormal heart rhythm has been recorded. The use of the recorder is neither automatic nor autonomic, and therefore requires either the subject to be conscious or another person's intervention.

Another known type of implantable monitoring device is a transponder-type device, in which a transponder is implanted in a patient and is subsequently accessed with a hand-held electromagnetic reader in a non-invasive manner. An example of the latter type of device is described in U.S. Pat. No. 5,833,603.

In many circumstances, medical personnel are interested in collecting a variety of different types of data relating to the behaviour of the heart and the condition of the patient. Moreover, as mentioned above, it is desirable to obtain as much relevant data as possible without requiring the patient to visit health care provider. Relevant information may include the oxygen saturation level of blood flowing through the aorta, blood pressure, heart rate, blood flow, stroke volume, cardiac output, the electrical activity of the heart (for generating electrocardiogram (ECG) data), and body temperature.

An integrated heart monitoring device for acquiring signals and transmitting data is disclosed herein. In one embodiment of the invention, the monitoring device includes an optical sensor assembly including a plurality of photon emitters and a plurality of photon detectors for detecting a plurality of optical signals. The emitters and detectors face the aorta. A computing device operates the plurality of emitters and detectors and processes the plurality of optical signals to obtain optical measurement values representing the location and size of the aorta and the oxygen saturation of the blood flowing through the aorta.

The monitoring device further includes a Doppler sensor for emitting and detecting a plurality of ultrasonic waves. The computing device also operates the Doppler sensor and, with the aid of the optical measurement values obtained using the optical sensor assembly, processes the plurality of ultrasonic waves to obtain Doppler measurement values representing heart rate, blood flow, stroke volume, blood pressure, and cardiac output.

The monitoring device further includes an ECG sensor for detecting the electrical signals which cause the heart to pump. Additionally, the monitoring device includes a temperature sensor for measuring the temperature of the patient. An energy storage device powers the computing device, the various sensors, and a communication device which is configured to transmit the collected data, or information relating to the collected data, according to a predetermined schedule or upon the occurrence of an event, such as abnormal data or a request for data from an external device. The sensors, the computing device, the communication device, and the energy storage device are enclosed in a housing, which may be worn by the patient or implanted.

By integrating the plurality of sensors and other components mentioned above, embodiments of the present invention permit a single device, mounted at one location on the patient's body, to accurately measure a comprehensive set of parameters relating to the behaviour of the heart, including cardiac output. Moreover, the integrated monitoring device described herein may perform analyses of the parameters and perform functions in response to the "on-board" analyses, as opposed to other sensing devices that export raw data for analysis by another device. As indicated above, the integrated monitoring device according to embodiments of the invention also communicates with other devices, wirelessly or otherwise, providing information and receiving commands and data. As such, the monitoring device collects, analyzes, and communicates data without any human intervention.

The features of this invention, and the manner of attaining them, will become more apparent and the invention itself will be better understood by reference to the following description of embodiments of the invention taken in conjunction with the accompanying drawings.

Corresponding reference characters indicate corresponding parts throughout the several views. Although the drawings represent embodiments of the present invention, the drawings are not necessarily to scale and certain features may be exaggerated in order to better illustrate and explain the present invention. The exemplifications set out herein illustrate embodiments of the invention in several forms and such exemplification is not to be construed as limiting the scope of the invention in any manner.

DETAILED DESCRIPTION OF EMBODIMENTS OF THE INVENTION

The embodiments discussed below are not intended to be exhaustive or limit the invention to the precise forms disclosed in the following detailed description. Rather, the embodiments are chosen and described so that others skilled in the art may utilize their teachings.

Figure 1A:
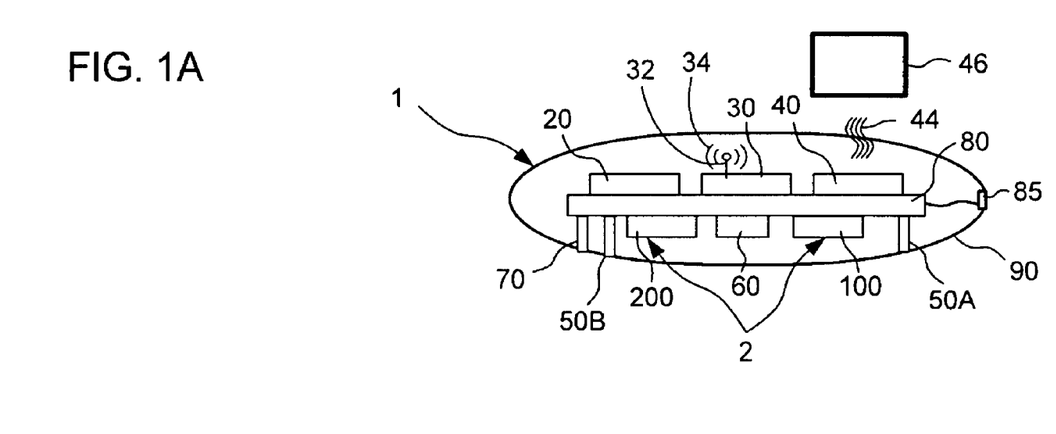
FIG. 1A is a schematic side view of a monitoring device according to one embodiment of the invention.

FIG. 1A depicts an integrated monitoring device according to one embodiment of the present invention. The monitoring device 1 generally includes a plurality of components including an optical sensor assembly 2, a Doppler sensor 60, an ECG sensor including probes 50A and 50B (hereinafter collectively referred to as ECG sensor 50), a temperature sensor 70, a computing device 20, a communication device 30, and an energy storage device 40, each of the components mounted on a board 80 and being in electronic communication with computing device 20. The components are enclosed in a housing 90.

Throughout this application, references made to optical sensor assembly 2 refer to the optical sensor assembly 2 described in the Optical Sensor Apparatus application incorporated herein by reference above. Also, references to the Doppler sensor 60 refer to the Doppler sensor 60 described in the Doppler Motion Sensor application incorporated by reference above. The full description of optical sensor assembly 2 and Doppler sensor 60 will not be repeated in this application.

In one embodiment according to the invention, monitoring device 1 is adapted to measure the physiological behaviour of a patient's heart. By "patient" it is meant a person or animal. Although the invention disclosed herein is described in the medical context, the teachings disclosed herein may be applicable in other contexts where compact data acquisition assemblies are desirable to perform measurements over time.

In one embodiment according to the invention, monitoring device 1 is implanted subcutaneously in the patient's body. It should be understood, however, that monitoring device 1 may be implanted at different locations using various implantation techniques. For example, monitoring device 1 may be implanted within the chest cavity beneath the rib cage. Housing 90 may be formed in the shape of a circular or oval disc, with dimensions roughly the same as two stacked quarter dollar coins. More specifically, housing 90 may be approximately three centimetres in diameter and approximately one centimetre thick. Of course, housing 90 may be configured in a variety of other shapes and sizes, depending upon the application. Housing 90 may include four outwardly projecting loops 92, shown in FIGS. 1B and 1C, for receiving sutures in order to fix the assembly subcutaneously within the patient's body. More or fewer loops 92 may be provided depending upon the shape of housing 90. When so fixed, optical sensor assembly 2, Doppler sensor 60, ECG sensor 50, and temperature sensor 70 are positioned facing inwardly while an energy coupler 42, which is described with particularity below, faces outwardly.

In another embodiment of a monitoring device 1 according to the invention, monitoring device 1 is integrated with an implanted cardiac device such as a pacemaker, a Cardiac Resynchronization Therapy (CRT) device, an implantable cardioverter defibrillator (ICD), etc. In such an embodiment, monitoring device 1 may communicate with the implanted cardiac device and provide information from the implanted cardiac device as well as from its own sensors to external devices in the manner described in the System for Monitoring application incorporated herein by reference above. As many implanted cardiac devices are currently well-understood and routinely prescribed, integration of monitoring device 1 into such other devices may provide an effective means for achieving market acceptance.

The above-described integration may be achieved by combining the components of monitoring device 1 and the cardiac device. If the cardiac device includes a computing device, for example, the algorithms that carry out the functions according to the invention may be incorporated with the computing device of the cardiac device instead of adding a second computing device. In a similar manner, energy storage and communication devices may be combined to avoid duplication and lower cost. In one embodiment, some components of monitoring device 1 are included within housing 90 and some components are included with the cardiac device. The cardiac device and the components in housing 90 are operably connected.

In another embodiment, monitoring device 1 is positioned externally to the patient's body. A support member is provided to support monitoring device 1 externally to the body. The support member may be permanently or temporarily coupled to monitoring device 1. In one embodiment, the support member comprises an adhesive layer for adhesively coupling the support member to the patient's body. In another embodiment, the support member comprises a belt, which may be elastic, for holding monitoring device 1 against the patient's body.

Monitoring device 1 may be implanted or positioned on the patient with the aid of an external mapping system such as an ultrasound machine. Proper placement ensures that the aorta is located within the sensing range of the various sensors of monitoring device 1. For example, monitoring device 1 may be positioned on the chest or back of the patient in a location that reduces interference by the ribs of the measurements acquired in the manner described herein.

1. Optical Sensor

As described in full detail in the Optical Sensor Apparatus application, optical sensor assembly 2, among other things, senses the oxygen saturation level of the patient's blood conveyed through the aorta. Sensing assembly 2 emits beams of electromagnetic energy in the infrared (IR) range of the electromagnetic spectrum and detects IR signals reflected from haemoglobin in the aorta, which is the iron-containing oxygen-transport metalloprotein in red blood cells.

Figure 2:
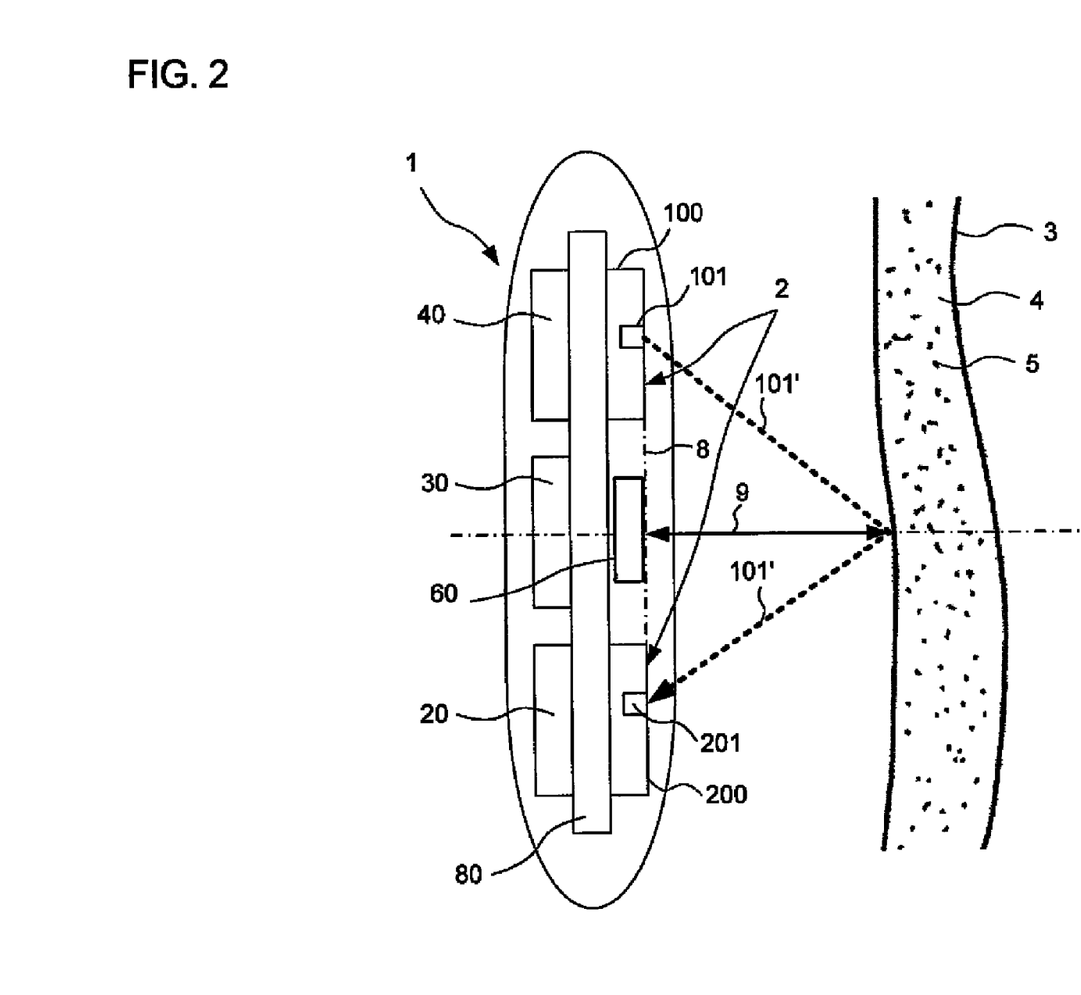
FIG. 2 is a schematic side view of the monitoring device of FIG. 1 and a vessel.

FIG. 2 illustrates the relationship between the aorta 3 conveying blood 4 having haemoglobin in red blood cells 5 and a pair of photocells, emitter 101 and detector 201, included in emitter array 100 and detector array 200 of sensor assembly 2, respectively. Emitter array 100 may include sixteen emitters 101-116 (only emitter 101 is shown) and detector array 200 may include sixteen detectors 201-216 (only detector 201 is shown), each being paired with an emitter. Sensor assembly 2 and arrays 100, 200 may be selected from the 8572 family of optical sensors manufactured by Motorola. Emitter 101 emits a beam of photons, including photon 101', some of which pass through aorta 3, and others of which are reflected off of red blood cells 5, including photon 101'. As described in the Optical Sensor Apparatus application, computing device 20 controls the operation of emitter 101 and measures the time required for detector 201 to detect the reflected beam, and interprets signals provided by detector 201 to determine the power or intensity of the reflected beam. This information, along with the known characteristics of the emitted beam, permits computing device 20 to determine a variety of characteristics of aorta 3 and blood 4.

According to one embodiment of the invention, computing device 20 processes signals received from detector array 200 to calculate the time required for the emitted beam to travel from the emitter, to the aorta 3, and to the detector as a reflected beam. As the speed of the beam is known and the distance between the emitter and detector is known, a simple calculation yields the distance from monitoring device 1 to the aorta 3. Computing device 20 also uses the signals from detector array 200 to determine the power of the reflected beam received by each detector in detector array 200. These power values are then used to determine the diameter of aorta 3 using the methods and principles described in the Optical Sensor Apparatus application.

It should be understood that in determining the diameter of the aorta in the manner described above, each of emitters 101-116 are activated individually, in rapid succession. In one embodiment of the invention, the beams are emitted individually in a row-by-row scanning fashion, beginning with emitter 101, which is followed sequentially until emitter 116 is activated. In other embodiments, other sequences are followed.

As indicated above, optical sensor assembly 2 also provides monitoring device 1 with the ability to determine the oxygen saturation level of blood carried by the aorta. When making an oxygen saturation measurement, sensing device 1 activates all emitters 101-116 of emitter array 100 simultaneously. Having already determined the size and location of the aorta as described above, the expected size or area of the reflected beam received by detector array 200 may be computed by computing device 20. The intensity or power of the reflected beam is, however, unknown prior to this measurement. Detector array 200 receives the reflected beam and provides a signal indicating the intensity of the reflected beam. As the intensity of the emitted beam is known, the intensity measurement of the reflected beam permits computation of the oxygen saturation percentage of the blood in the aorta. Under normal operating conditions, monitoring device 1 may perform an oxygen saturation measurement once or twice per day.

In one embodiment, monitoring device 1 also calculates cardiac pulse. As discussed previously, detectors 201-216 produce power signals representative of iron content in blood. As the heart pumps oxygenated blood through the aorta, the power signals fluctuate. A plurality of power signals may be obtained in rapid succession to capture the power measurement fluctuation. More specifically, by performing many oxygen saturation measurements (e.g., ten times per second), over a period of time (e.g., fifteen seconds), the saturation measurements will exhibit a pattern or periodicity that represents the beating of the heart. Computing device 20 may determine a curve to fit the saturation measurements, such as a sinusoidal curve, which corresponds directly to the cardiac cycle. Computing device 20 may determine the frequency of peak values of the curve to determine its period. Each period represents a cardiac cycle. By multiplying the number of cardiac cycles in the sample period (e.g., fifteen seconds) by an appropriate factor, computing device 20 may determine pulse rate in terms of cardiac cycles per minute. In one embodiment, computing device 20 stores cardiac pulse values as normal reference values and detects an abnormal or irregular cardiac rhythm by comparing cardiac pulse values to reference values.

2. Doppler Sensor

In an embodiment where monitoring device 1 includes Doppler sensor 60, aorta diameter and location provided by optical sensor assembly 2 may be used to calculate the velocity of blood flowing through the aorta, the volume of blood flowing through the aorta, the patient's blood pressure, and the cardiac output. These parameters may be used to calculate and diagnose an abnormal condition relating to cardiac output. As is fully described in the Doppler Motion Sensor application referenced above, one embodiment of Doppler sensor 60 includes three transducers for insonating the aorta and receiving reflected ultrasonic waves. The velocity of the blood in the aorta is determined by directing the ultrasonic waves towards the blood at a known angle, measuring the frequency shift of the reflected ultrasound energy, and then calculating the velocity of the blood. More specifically, the Doppler frequency shift is proportional to the component of the velocity vector that is parallel to the insonifying wave. The velocity v of the blood is determined by the following equation:

$$v = f_d \cdot c / (2 \cdot f \cdot \cos \theta)$$

where c is the velocity of sound in blood, f is the frequency of the insonifying wave, θ is the angle between the wave and the velocity vector, and $f_d$ is Doppler frequency shift.

Doppler sensor 60, which may be a continuous wave sensor or a pulsed wave sensor, measures frequency shift by comparing phase shifts between subsequently received waves according to principles that are well known in the art. As the distance between Doppler sensor 60 and the aorta has already been determined by optical sensor assembly 2, and the speed of sound through tissue is known, the frequency shift permits computing device 20 to determine the actual velocity of blood in the aorta.

Figure 3:
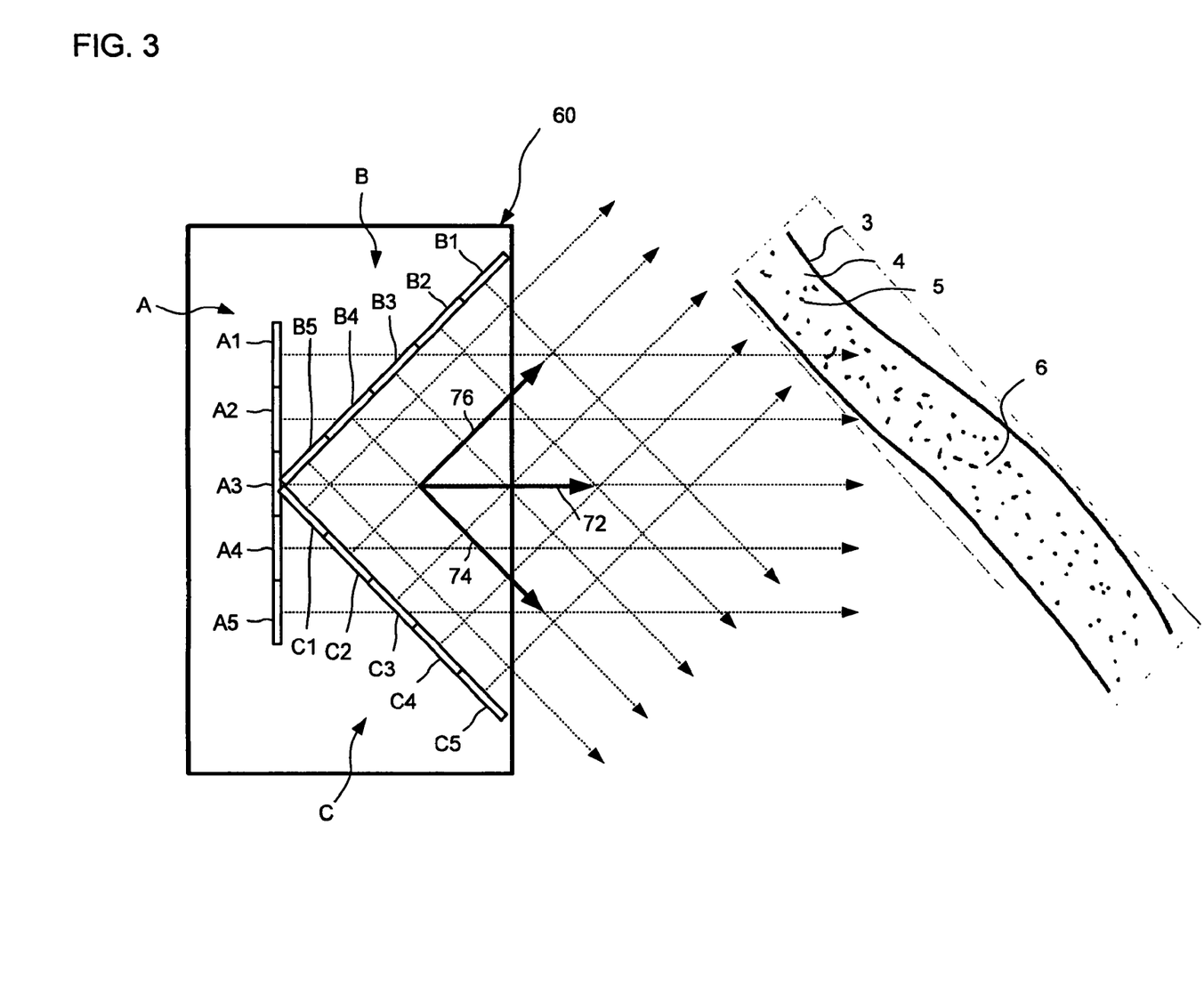
FIG. 3 is a schematic side view of a Doppler sensor according to one embodiment of the invention.

FIG. 3 illustrates Doppler sensor 60 including linear array transducers A, B and C according to one embodiment of the invention. Each of transducers A, B and C is operably connected with a driver device (not shown) that powers the transducer. Transducers A, B and C are disposed at an angle relative to each other. Transducers B and C are disposed at a 45 degree angle relative to transducer A and at 90 degrees relative to each other. Other relative angles among the transducers may be used. Each of transducers A, B and C may be driven at a different frequency to distinguish the source of the reflected waves received by Doppler sensor 60. For convenience, each transducer in a linear array is referred to herein as a transducer segment. In the embodiment shown, each linear array transducer comprises five transducer segments. Transducer segments may be operably connected to be activated separately or concurrently. Separate activation of one or more transducer segments is desirable to limit power consumption.

As shown, transducer A includes segments A1-A5, transducer B includes segments B1-B5, and transducer C includes segments C1-C5. Each segment may transmit and receive ultrasonic energy in the form of waves. The arrows originating at each segment and projecting perpendicularly to the segment represent the direction of waves transmitted by each segment. Further, arrows 72, 74, and 76 represents the directions of waves produced by transducers A, B and C, in aggregate, respectively. In one embodiment, one or more segments of transducer A are energized at a frequency of 5 Mhz, one or more segments of transducer B are energized at a frequency of 4.5 Mhz, and one or more segments of transducer C are energized at a frequency of 5.5 Mhz. Frequency selection is a function of the distance between the transducer and the target fluid and is selected accordingly. A reflected wave may be measured at each segment of a linear array transducer. Each segment may be energized sequentially and may be energized a plurality of times.

The Doppler shift, or frequency shift, is proportional to the component of the velocity vector parallel to the impinging wave. Since the Doppler shift depends from the cosine of the angle $\theta$ between the wave and the velocity vector, and the cosine function ranges between 0 and 1, signals produced by waves oriented parallel to the velocity vector produce selected signals and, as the angle $\theta$ increases, it becomes increasingly more difficult to determine the Doppler shift from those signals. As is fully described in the Doppler Motion Sensor application, the K-shape arrangement of transducers A, B, C ensures that at least one of the transducers is oriented at an acceptable angle $\theta$. Three transducers enable Doppler sensor 60 to obtain a sufficient number of signals even when the relative position of Doppler sensor 60 and aorta 3 change slightly with time or other factors such as a patient's activity level and posture. When broad waves are transmitted, reflected waves may be received by each transducer. However, since waves have frequencies corresponding to each transmitting transducer, Doppler sensor 60 is able to select which signals to filter based on the relative position of the corresponding transmitting transducer and its transmission frequency.

As discussed previously, the calculation of blood velocity requires knowledge of the incident angle $\theta$ between the emitted waves and aorta 3. Incident angle and other data characterizing the relative position of aorta 3 and Doppler sensor 60 may be obtained in various ways. Once obtained, it may be stored in memory 26 (see FIG. 6) as reference values. In one embodiment, the relative position data is provided to computing device 20 by optical sensor assembly 2. With this information, computing device 20 computes a blood velocity value by comparing the frequency of the transmitted and the received waves according to well known frequency-shift and angle algorithms or tables.

The velocity of the blood flowing through the aorta is different depending upon which portions of the blood are being measured. According to well-understood principles of fluid dynamics, fluid flowing near the outer wall of a vessel flows more slowly than fluid flowing through the central axis of the vessel because of shear stresses between the fluid and the outer wall. The distance and diameter measurements provided by optical sensor apparatus 2 permit computing device 20 to determine, from the measurements of Doppler sensor 60, the location of aorta 3 within the reflected wave detected by Doppler sensor 60. Each of the five velocity measurements in each of the three sets of measurements taken in the manner described in the Doppler Motion Sensor application is averaged to determine an approximate overall blood flow through aorta 3 and to account for the velocity profile across the diameter of aorta 3. The sets of velocity measurements are taken at the maximum (systolic) and minimum (diastolic) flow conditions of the cardiac cycle. Accordingly, by averaging the five velocity measurements for each of the three sets of maximum flow measurements, and averaging the three results from those calculations, computing device 20 determines an average maximum flow measurement. An average minimum flow measurement is computed in a similar fashion. Finally, the average minimum and average maximum blood flow measurements are averaged to determine the mean blood flow for the patient.

Next, computing device 20 may compute stroke volume by simply multiplying the mean blood flow measurement described above by the area of aorta 3 (i.e., mean blood flow*$\pi r^2$), where r is the radius of aorta 3. Of course, the radius of aorta 3 is simply one half of the aorta diameter, which is determined using optical sensor assembly 2 in the manner described above.

3. ECG Sensor

ECG sensor 50 is, in one embodiment of the invention, a single lead device including an anode probe 50A and a cathode probe 50B (collectively referred to herein as "ECG sensor 50"). ECG sensor 50 uses probes 50A, 50B to detect changes in voltage of the electrical impulses provided to the heart muscles. As is well understood in the art, these electrical signals which trigger heart beats normally start at the top of the heart in the right atrium, and travel from the top of the heart to the bottom. They cause the heart muscle to contract as they travel through the heart. As the heart contracts, it pumps blood out to the rest of the body. By monitoring the electrical activity of the heart over time, ECG sensor 50 permits computing device 20 to determine how fast the heart is beating (i.e., pulse) by determining the number of cardiac cycles per minute (or fraction of a minute). The pulse measurement may be used with the stroke volume discussed above to determine cardiac output. More specifically, the stroke volume measurement may be multiplied by the number of strokes per minute (i.e., pulse) to determine the total volume of blood displaced per minute (i.e., cardiac output).

In one embodiment of the invention, the pulse measured by ECG sensor 50 is compared to the pulse measured by optical sensor assembly 2 as described in the Optical Sensor Apparatus application. If the measurements differ by more than a predetermined amount, the ECG pulse measurement may be discarded under the assumption that electrical interference or some other disturbance caused errors in the detected signals.

In this manner, optical sensor assembly 2 functions as a backup pulse measurement device for ECG sensor 50.

ECG sensor 50 provides voltage measurements to computing device 20, which in turn processes the data by filtering out frequencies outside the known range of frequencies generated by the heart's electrical activity. ECG sensor 50 is also mounted within housing 90 in a manner and location that electrically isolates ECG sensor 50 from the other electronic components of monitoring device 1 to minimize the electrical interference caused by those other electronic devices. In one embodiment of the invention, the output of ECG sensor 50 is passed through a band pass filter having a lower cut-off frequency and an upper cut-off frequency. Additionally, computing device 20 may further process the data to produce a smooth ECG trace by applying any of a number of suitable digital smoothing functions.

The output of ECG sensor 50 also permits computing device 20 to identify the maximum and minimum blood flow through the aorta, which are used in the stroke volume and cardiac output calculations described above. Additionally, It shows the heart's rhythm (steady or irregular) and where in the body the heart beat is being recorded. It also records the strength and timing of the electrical signals as they pass through each part of the heart.

Figure 4:
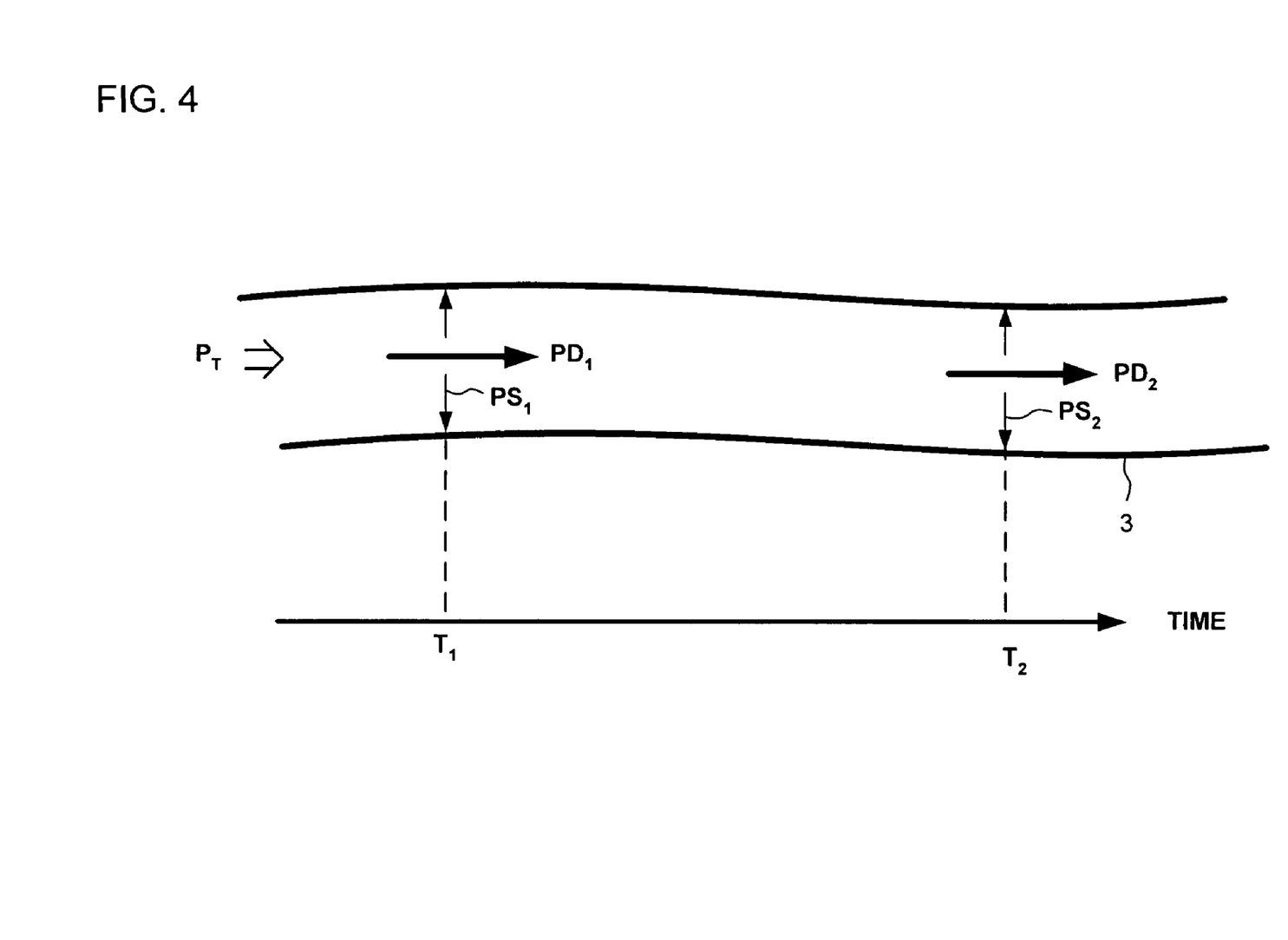
FIG. 4 is a conceptual view of fluid flowing through a vessel.

Referring now to FIG. 4, ECG sensor 50 and Doppler sensor 60 are used in combination to determine the blood pressure of the patient directly from the aorta 3. One skilled in the art may, using the ECG trace provided by ECG sensor 50, determine with accuracy the maximum blood flow position of the cardiac cycle and the minimum blood flow position. Doppler sensor 60 facilitates determination of the speed or velocity of blood in aorta 3 under the maximum and minimum blood flow conditions in the manner described above. Computing device 20 converts the velocity measurements under each condition into pressure measurements using the known internal surface area of aorta 3 (determined from the diameter measurements facilitated by optical sensor assembly 2) according to principles dictated by Bernoulli's equation. These pressure measurements reflect the dynamic pressure of the blood flowing through aorta 3 under the maximum and minimum flow conditions. More specifically, at $T_1$ of FIG. 4, the dynamic pressure $PD_1$ corresponds to the pressure determined from the velocity measurements taken under maximum blood flow conditions. At $T_2$, $PD_2$ corresponds to the pressure determined from the velocity measurements taken under minimum blood flow conditions. It is well known that the total pressure of a fluid flowing through a vessel is the sum of the dynamic pressure and the static pressure. In the case of the aorta 3, the static pressure (depicted as force arrows directed outwardly against the outer wall of the aorta 3) under maximum flow conditions ($PS_1$) directly corresponds to the systolic blood pressure measurement and the static pressure under minimum flow conditions ($PS_2$) directly corresponds to the diastolic blood pressure measurement.

The systolic and diastolic blood pressure measurements may be derived by further computing the total pressure (PT) of blood flowing through aorta 3 and taking advantage of the fact that the total pressure through the aorta at $T_1$ (i.e., $PT_1$) must be the same as the total pressure at $T_2$ (i.e., $PT_2$). Total pressure is derived by computing the change in pressure from the minimum flow conditions to the maximum flow conditions. This change or acceleration, in conjunction with the stroke volume and the known elasticity of aorta 3, permits computing device 20 to determine total pressure according to well known principles in the art. Thus, at time $T_1$, the equation $PT_1 = PS_1 + PD_1$ may be solved for $PS_1$ and at time $T_2$, the equation $PT_2 = PS_2 + PD_2$ may be solved for $PS_2$. As indicated above, $PS_1$ and $PS_2$ are the systolic and diastolic blood pressure measurements, respectively.

It should be understood that although the blood pressure computation described above refers to determining blood pressure in aorta 3, the same process may be carried out to determine blood pressure in the pulmonary artery, assuming the pulmonary artery is within the sensing range of monitoring device 1. As described in the Optical Sensor Apparatus application, monitoring device 1 distinguishes between the pulmonary artery and aorta 3 by measuring the oxygen saturation of both, and determining which vessel carries blood with higher oxygen saturation. That vessel must be aorta 3. In another embodiment of the invention, monitoring device 1 instead identifies the vessel with lower oxygen saturation as the vessel of interest (i.e., the pulmonary artery). The location and size of the pulmonary artery is then determined in the same manner as described with reference to aorta 3. With the geometry of the pulmonary artery defined, the pressure of the blood flowing through the pulmonary artery is measured as described above with reference to aorta 3.

In one embodiment of the invention shown in FIG. 1A, housing 90 includes a connector 85 to permit connection of additional ECG leads. Connector 85 is electrically coupled to ECG sensor 50 and other components of monitoring device 1 through board 80. When additional ECG leads are connected to connector 85, connector 85 passes signals from the additional leads to ECG sensor 50. As is known in the art, the additional leads may be affixed to various locations on the chest, back, arms, or legs of the patient, and each lead includes a receiver for detecting electrical activity. As indicated above, connector 85 may also function as a I/O port for monitoring device 1, permitting downloading of data to a docking station 304 and uploading of data and instructions during a programming operation.

4. Temperature Sensor

A variety of different devices may function as temperature sensor 70. Temperature sensor 70 is, in one embodiment of the invention, a readily available resistance temperature detector (RTD). In general, temperature sensor 70 may include a metallic component (wire wound or thin film) with the physical property of an electrical resistance which varies with changes in temperature. Typically, the higher the temperature in the environment of temperature sensor 70, the greater the electrical resistance across the metallic component of temperature sensor 70. Temperature sensors having a platinum metallic component may be desirable because of the nearly linear relationship between resistance and temperature platinum exhibits over a fairly wide temperature range. Of course, one skilled in the art could readily adapt a temperature sensor having a non-linear temperature/resistance curve, so long as the sensor's behaviour over the temperature range of interest is suitably repeatable.

Figure 5:
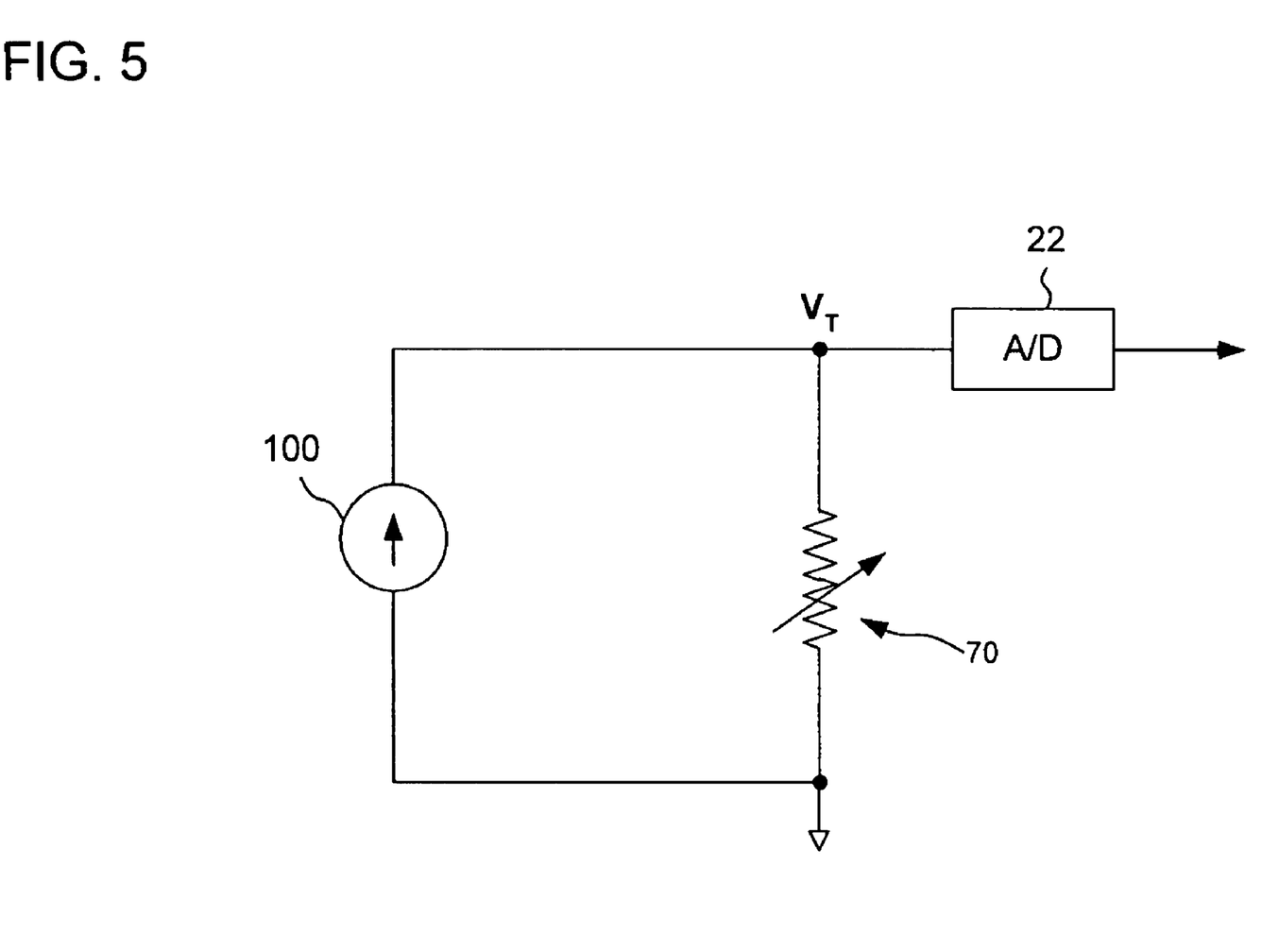
FIG. 5 is a schematic representation of a temperature sensing circuit.

As shown in FIG. 5, temperature sensor 70 is coupled to a constant current source 100, which is also located within housing 90. Current source 100 maintains a constant current through temperature sensor 70 as the resistance of temperature sensor 70 changes with temperature. Accordingly, the voltage across temperature sensor 70 ($V_T$) changes in direct proportion to the changes in temperature. More specifically, according to Ohm's law, Voltage=current*resistance. With a constant current source, changes in resistance due to temperature changes are detected as changes in $V_T$. In one embodiment of the invention, $V_T$ is passed through analog-to-digital converter 22, which is read by computing device 20. Computing device 20 then determines the measured temperature and stores the temperature measurement in memory 26.

It should be understood that although FIG. 5 depicts a constant-current, voltage measurement circuit for use in conjunction with temperature sensor 70, a variety of different circuits could readily be adapted for use with temperature sensor 70, including circuits that measure changes in current passing through temperature sensor 70.

Temperature sensor 70 is mounted within housing 90 such that the temperature sensitive component of temperature sensor 70 is adjacent the outer surface of housing 90, and substantially thermally isolated from any thermal energy that may be created by the operation of the other electronic components mounted within housing 90. In this way, temperature sensor 70 is positioned to detect temperature changes in the body of the patient (either when monitoring device 1 is implanted or when it is worn by the patient) as opposed to changes in temperature of the electronics of monitoring device 1. It should be understood, however, that temperature sensor 70 may also be calibrated to compensate for changes in detected temperature due to thermal energy from monitoring device 1. Memory 26 of computing device 20 includes a look-up table relating the digital voltage across temperature sensor 70 to temperature, according to the specified operational characteristics of temperature sensor 70. Computing device 20 periodically reads the digital voltage signal, accesses the look-up table in memory 26, and determines the current body temperature of the patient. The temperature is stored in memory 26 and may be transmitted from monitoring device 1 in the manner described below with reference to communication device 30.

2. Computing Device

Figure 6:
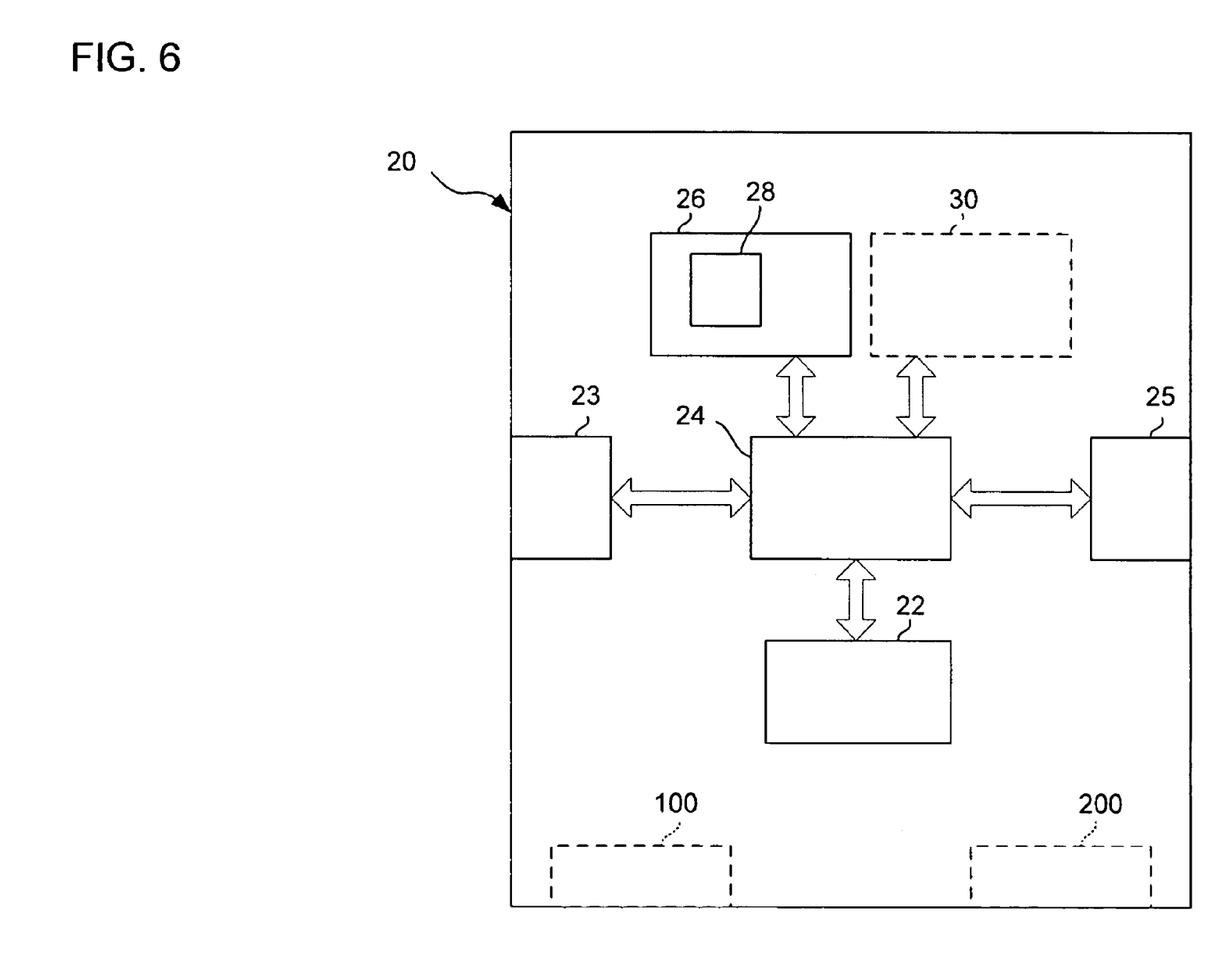
FIG. 6 is a conceptual view of a computing device according to one embodiment of the present invention.

Computing device 20 comprises a plurality of components. While components are described herein as if they were independent components, the components may be combined in a single device such as an application specific integrated circuit. As shown in FIG. 6, computing device 20 includes an A/D converter 22 (which also converts optical signals to digital signals), a processor 24, a memory 26, a program 28, inputs 23, and outputs 25. Memory 26 may include, but is not limited to, RAM, ROM, EEPROM, flash memory or other memory technology. A/D converter 22, processor 24 and memory 26 may be constructed in an integrated circuit. The integrated circuit may further include emitter array 100, detector array 200, and communication device 30.

Program 28 represents computer instructions directing processor 24 to perform tasks responsive to data. Program 28 resides in memory 26. Data, including reference data and measurement data, also resides in memory 26. Reference data may be stored in ROM or it may be stored in RAM so that it may be modified over time, either in response to external inputs or in response to characteristics of measurement data collected over time. Protocols for responding to measurement values may also be provided. Protocols may be stored in permanent memory or may be stored in non-permanent memory such as RAM and are described in further detail in the System for Monitoring application reference above.

Figure 7:
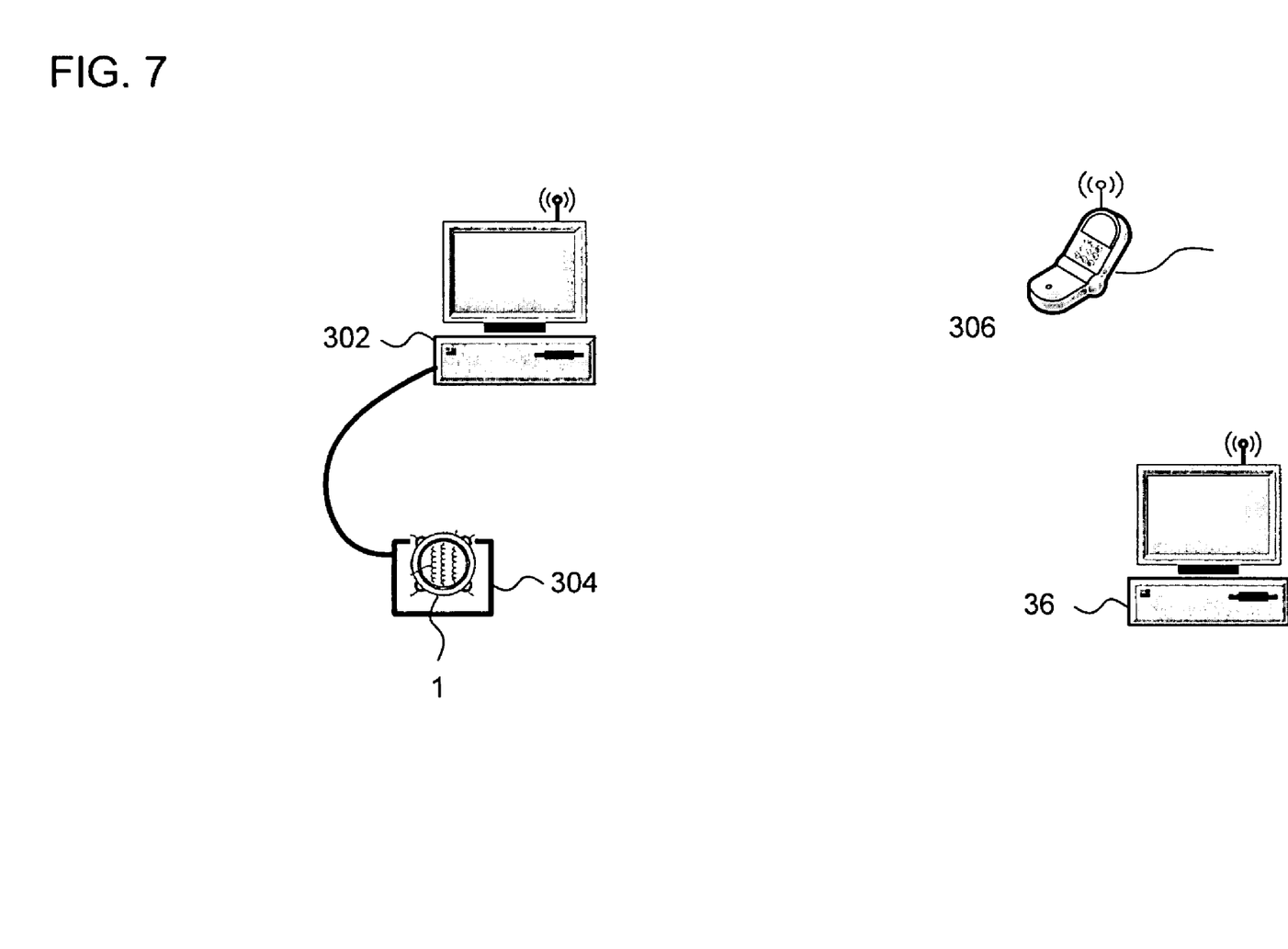
FIG. 7 is a conceptual view of a system adapted to transmit and receive communication signals from the monitoring device of FIG. 1.

Computing device 20 may be configured to cause communication device 30 to transmit an alert if an abnormal condition is detected, particularly a condition determined to be a serious or dangerous condition according to a prescribed protocol. The alert may be used to actuate an alarm or to alert the patient to take remedial action. A remedial action may be terminating or reducing physical activity. The alert may also provide global positioning (GPS) information to an emergency service. Referring to FIG. 7, the abnormal condition, when found to be present, may also be displayed on a computer 36 and/or transmitted via communication device 30 to a caregiver. The alert may comprise a text message or a code corresponding to the condition. Computing device 20 may also initiate a new measurement cycle and measure on a continuous basis in response to the detection of an abnormal condition.

Computing device 20 may also initiate a treatment. Monitoring device 1 may receive, through communication device 30, an external command to perform a treatment in response to the alert. Optionally, based on the protocol, an abnormal condition may also be used to direct a device adapted to provide treatment to deliver such treatment. Treatment may include, for example, an electric shock or a drug delivery.

Parameter values and/or other information may be communicated to an external device. The parameter values may be stored in memory 26 and transmitted wirelessly by communication device 30. The communication signal from communication device 30 may be activated on a periodic basis (e.g., once per day, once per week, etc.), in response to an abnormal condition, in response to an externally received command, whenever memory usage exceeds a predetermined amount, or whenever the energy storage level is determined to be low, the latter two conditions established to prevent data loss as a result of memory overflow or energy loss. It should also be understood that monitoring device 1 may include communication devices in addition to communication device 30. For example, where communication device 30 is a cellular modem, monitoring device 1 may also include a backup Bluetooth or RF communication device. Such a backup device may be desirable in situations where, after one or more attempts, it becomes apparent that the cellular modem is unable to transmit information (e.g., due to low available power, poor network coverage, etc.). In such a situation, computing device 20 may activate the backup communication device to transmit information or an alert to an alternate external receiving device.

Alternatively or in addition to the above-described transmissions, computing device 20 may be programmed to respond to requests for data received by communication device 30 (e.g., from a health care provider) by causing communication device 30 to transmit the requested data or information representing the requested data.

The communication signal may be received by equipment near the patient to alert the patient to the condition, or received remotely (such as over a network) by a healthcare provider, relative, or other predetermined recipient. Further description of a networked system including at least some of the principles of the present invention is provided in the System for Monitoring application reference above.

3. Communication Device

In one embodiment of the invention, communication device 30 is a two-way communication device, e.g. via the cellular telephone system and/or the GPS satellite system, such as NOKIA model number KNL1147-V. In an alternate embodiment, communication device 30 is capable of transmitting information, but does not receive information or commands. As shown in FIG. 1A, communication device 30 includes an antenna 32 for transmitting and receiving communication signals. The communication signals, represented by symbol 34, travel wirelessly to and from one of a plurality of optional external communication devices.

Referring again to FIG. 7, an external communication device may be a computer 302 or any electronic device capable of wirelessly receiving a communication signal, such as telephone 306 which is exemplified as a cellular phone. By communication signal is meant a signal that has one or more of its characteristics set or changed to encode information in the signal. By way of example, and not limitation, communication signals include acoustic, RF, infrared, other wireless media, and combinations of any of the above. An external communication device may also be a relay unit located externally of the patient's body, e.g. clipped to the patient's belt. The relay unit may include a receiver for receiving the transmissions from communication device 30, and a transmitter for re-transmitting the communication signal to another external communication device. The relay unit may also be stationary and hardwired for connection to the internet or direct connection to a healthcare provider's computer. Likewise, the relay unit may receive a communication signal from a healthcare provider and transmit the signal to communication device 30.

4. Energy Storage Device

Referring again to FIGS. 1A-1C, a system for recharging energy storage device 40 may be provided in one embodiment according to the invention. Computing device 20 receives energy from energy storage device 40. Energy storage device 40 includes an energy storage component such as a battery. Optionally, monitoring device 1 may also include an energy coupler for receiving energy from an external source to charge energy storage device 40.

Figure 1B:
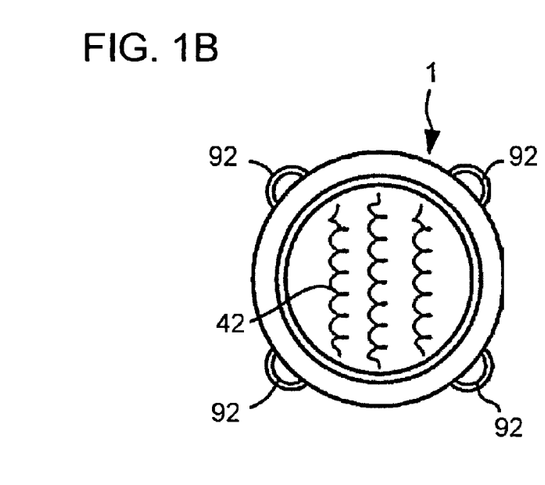
FIG. 1B is an outwardly-facing view of the monitoring device of FIG. 1.
Figure 1C:
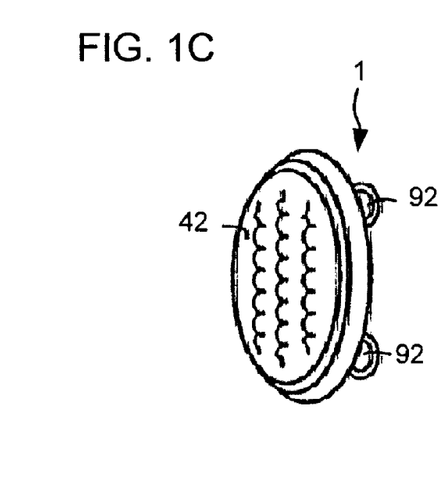
FIG. 1C is a perspective view of the monitoring device of FIG. 1.

One example of an energy coupler is an electromagnetic device, such as induction coils 42, for receiving external electromagnetic signals 44 and converting such signals into electrical energy for recharging the energy storage component. An external electromagnetic device 46 generates electromagnetic signal 44 which is received and converted into electrical energy by energy storage device 40. Energy storage device 40 may provide a charge signal to computing device 20. Computing device 20 may compare the charge signal to a reference charge signal and initiate a low charge communication signal for alerting the patient and/or healthcare providers. Alternatively, a detector, such as a voltage sensor, may be used to monitor the charge of energy storage device 40 and provide a signal to computing device 20 when the charge falls below a threshold. Electromagnetic device 46 may be placed near monitoring device 1 to charge energy storage device 40.

Energy may instead, or additionally, be provided in the form of ultrasonic vibrations. For example, a piezoelectric transducer may be included in monitoring device 1. An ultrasonic vibration may be provided externally. The transducer generates electricity when driven by ultrasonic vibrations. As indicated herein, energy or power may also be provided to monitoring device 1 through connector 85.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains. For example, it should be understood that each of or some of optical sensor assembly 2, Doppler sensor 60, ECG sensor 50, and temperature sensor 70 may be modular in design. As such, a plurality of different Doppler sensors 60, for example, may be produced to have different performance characteristics (e.g., different output frequencies). Depending upon the application, any of the plurality of the sensors may be installed in monitoring device 1 to achieve the desired performance. Once monitoring device 1 is equipped with the selected sensors, computing device 20 may be programmed to adapt the various algorithms to accommodate the selected sensors. In this manner, a basic monitoring device 1 including computing device 20, communication device 30, etc., may be "custom" built with any of a variety of sensors and programmed to operate with the selected sensors.

As another example, it should be understood that while optical sensor assembly 2, Doppler sensor 60, and temperature sensor 70 are described herein as being activated to obtain measurements relatively infrequently (at least under normal conditions) to conserve power, as battery technology improves, the frequency of activation of these sensors may be increased. Also, where monitoring device 1 is worn externally, connector 85 may be used to supply power to monitoring device 1, thereby eliminating the power consumption concern and permitting frequent, or even continuous, operation of these sensors.

What is claimed is:

1. A device for monitoring the heart of a patient, including:
a housing;
a computing device mounted within the housing;
an optical sensor mounted within the housing and adapted to provide signals to the computing device sufficient to compute a distance from the optical sensor to a vessel carrying blood, as well a diameter of the vessel;
a Doppler sensor mounted within the housing and adapted to direct ultrasonic waves based on the distance and diameter, and to provide signals to the computing device indicative of a velocity of the blood through the vessel; and
an ECG sensor mounted within the housing and adapted to provide signals to the computing device indicative of a plurality of electrical stimuli that cause the heart to pump;
the computing device using signals from the optical sensor, the Doppler sensor, and the ECG sensor to compute parameters including oxygen saturation of the blood, blood flow, blood pressure, heart rate, and cardiac output.

2. The device of claim 1, further including a temperature sensor mounted within the housing and adapted to provide signals to the computing device indicative of a temperature of the patient.

3. The device of claim 1, further including a communication device mounted within the housing, the communication device being coupled to the computing device and configured to transmit information relating to the parameters.

4. The device of claim 1, wherein the housing is configured for subcutaneous implantation.

5. The device of claim 1, wherein timing of the operation of the Doppler sensor is based on the signals from the ECG sensor.

6. The device of claim 1, wherein the optical sensor includes an emitter array and a detector array.

7. The device of claim 1, further including a connector mounted to the housing, the connector being adapted to couple to ECG leads.

8. The device of claim 7, wherein the connector is configured to enable one of programming of the computing device and downloading information relating to the parameters.

9. A monitoring device for measuring parameters indicative of behavior of the heart of a patient, the device including:
a plurality of sensors mounted within an implantable housing, the plurality of sensors including
an optical sensor for measuring oxygen saturation of blood flowing through a vessel, the optical sensor further configured to provide signals sufficient compute a distance from the optical sensor to a vessel carrying blood and a diameter of the vessel,
a Doppler sensor configured to direct ultrasonic waves to the vessel based on the distance and diameter and to receive corresponding frequency-shifted signals for measuring a velocity of the blood, an ECG sensor for measuring electrical activity of the heart, and a temperature sensor for measuring a temperature of the patient;

a communication device mounted within the housing, the communication device being configured to wirelessly transmit information relating to the measured parameters; and a computing device that executes a program to determine, based on signals from the plurality of sensors, blood pressure and cardiac output.

10. The monitoring device of claim 9, further including a rechargeable battery mounted within the housing to power the plurality of sensors, the communication device, and the computing device.

11. The monitoring device of claim 9, wherein the computing device activates the Doppler sensor at a first stage in a cardiac cycle corresponding to a maximum blood flow condition through the vessel, and at a second stage in the cardiac cycle corresponding to a minimum blood flow condition through the vessel.

12. The monitoring device of claim 11, wherein the computing device activates the Doppler sensor at the first stage and the second stage based on information received from the ECG sensor.

13. The monitoring device of claim 11, wherein the computing device activates the Doppler sensor a plurality of times at the first stage to obtain a plurality of first measurements, and a plurality of times at the second stage to obtain a plurality of second measurements, the computing device averaging the plurality of first measurements and the plurality of second measurements.

14. The monitoring device of claim 9, wherein the housing includes a plurality of loops to facilitate implantation.

15. The monitoring device of claim 9, wherein the optical sensor emits infrared beams toward the vessel and detects infrared beams reflected from red blood cells flowing through the vessel.

16. The monitoring device of claim 9, wherein the optical sensor includes an emitter array having a plurality of emitter cells and a detector array having a plurality of detector cells.

17. The monitoring device of claim 16, wherein all of the emitter cells emit beams simultaneously during the oxygen saturation measurement.

18. The monitoring device of claim 16, wherein the computing device activates each of the plurality of emitter cells individually and processes signals received from the detector cells to determine a distance from the optical sensor to the vessel and the diameter of the vessel.

19. The monitoring device of claim 9, wherein the Doppler sensor includes three transducers arranged in a K shape.

20. The monitoring device of claim 19, wherein each of the transducers emit waves of differing frequencies.

21. The monitoring device of claim 9, wherein the monitoring device is integrated with an implanted cardiac device.

22. The monitoring device of claim 9, wherein the vessel is an aorta.

23. The monitoring device of claim 9, wherein the vessel is a pulmonary artery.

* * * * *